United States Patent [19]

Ramp

[11] Patent Number: 4,892,818
[45] Date of Patent: Jan. 9, 1990

[54] BIOREACTOR

[76] Inventor: Floyd Ramp, 3948 Humphrey Rd., Richfield, Ohio 44286

[21] Appl. No.: 11,315

[22] Filed: Feb. 5, 1987

[51] Int. Cl.[4] ............................................. C12Q 1/24
[52] U.S. Cl. ........................................ 435/30; 435/3; 435/289
[58] Field of Search ............................. 435/287–300, 435/30; 422/144–147

[56] References Cited

U.S. PATENT DOCUMENTS

| | | | |
|---|---|---|---|
| 2,865,816 | 12/1958 | Stefanye et al. | 435/300 |
| 3,501,379 | 3/1970 | Tate | 435/300 |
| 4,453,574 | 6/1984 | Elliot | 435/287 |
| 4,683,062 | 7/1987 | Krovak et al. | 435/300 |

Primary Examiner—Barry S. Richman
Assistant Examiner—T. J. Wallen

[57] ABSTRACT

A bioreactor and method of its operation are described comprising a vertical column with a lower reaction section filled with column packing particles classifiable by means of their differential settling rates in a liquid, and an upper disengagement section, preferably of larger diameter and of equal or greater volume than the reaction section, the two sections desirably being connected by a transition section in the shape of an inverted, truncated cone. Following initial classification of the packing in the reaction section, the packing is inoculated with microorganisms, and the bioreaction commenced by introducing nutrient feed at one end of the column, and withdrawing product at the other end. The packing is periodically cleaned, as required, by dispersing it into the disengagement section by passing liquid at an increased velocity upward through the column until contaminants have been dislodged. The liquid velocity is thereupon decreased, and the packing reclassified in its original order in the reaction section. Zones of distinct microorganism colonies are thereby re-established, and the bioreaction is allowed to proceed by recommencing the feed of nutrients to the column.

7 Claims, 2 Drawing Sheets

BIOREACTOR

This invention relates to microbiological reactions, and to apparatuses and methods for carrying out such reactions. More particularly, this invention relates to apparatuses and methods for carrying out microbiological reactions in a continuous manner. Specifically, this invention relates to carrying out microbiological reactions in specially designed packed columns, as well as to processes related thereto, involving the removal of classified packing for regenerative cleaning and its subsequent repositioning in the initial classified condition so as to maintain the relative vertical orientation of specific microorganism colonies adhering thereto.

BACKGROUND OF THE INVENTION

Microbiological processes have been used by man throughout recorded history. Most societies, however, primitive, use a fermentation process to produce beverages containing ethanol. In addition, such compounds as acetic acid, acetone, n-butyl alcohol as well as formic, lactic, and propionoic acids are produced by microbiological processes. Materials of the type mentioned are important articles of commerce, both as such, and as a consequence of the derivatives and materials which can be produced therefrom.

Commonly, microbiological processes are carried out in batch processes in which a nutritive feed, in the case of wine, grape juice, is inoculated with the particular strain of microorganism selected, and the reaction is permitted to continue until the environment is for one reason or another no longer conductive to continuation of the reaction. Batch processes of the type described are slow, however, frequently produce erratic results, and they usually require large equipment.

Continuous processes, on the other hand, are noted for the uniformity of product which they are capable of producing, in addition to the speed with which they can be carried out. Furthermore, since continuous processes make high rates of production possible, smaller, normally less expensive equipment than in the case of batch processes may be employed to achieve the desired rate of production.

In the case of microbiological reactions, continuous processes may be carried out, for instance, in packed columns. Such equipment usually consists of cylindrical vessels filled with packing material such as beryl saddles, rasching rings, spheres and the like, the surface of which is innoculated by being exposed to the microorganism capable of carrying out the desired reaction. A nutrative feed is then introduced at one end of the column, allowed to proceed through the packing, and withdrawn at the other end in a continuous manner. A device of the type described, known as a "bioreactor", when operated under constant conditions of feed rates, temperatures, and the like, eventually results in separate and distinct colonies of microorganisms oriented in zones along its vertical height. For example, at the point in the column where the nutrative feed is introduced, it will be found that microorganisms in the vicinity will be of a type which are adapted to high concentrations of nutrients. Further along the column, organisms will be found which can thrive on a more dilute nutritive feed, in the presence of more product, while those still further along can operate with still less nutrients, and which are even better adapted to withstand high concentrations of the product produced by the bioreaction, for instance, high alcohol concentrations. The colonization of successive areas along the packed column with organisms uniquely adapted to the conditions at their location provides an unusually efficient reaction overall, since each zone of the column is populated by microorganisms best able to cope with the conditions existing at that point.

While bioreactors are theoretically uniquely suited to carrying out microbiological processes, they have an unfortunate tendency to clog eventually due to the build-up of the microorganisms and the debris associated therewith, on the packing material. Such a build-up eventually reduces the throughput of the column and changes the environment within the different zones. When plugging of the type described proceeds far enough, it becomes necessary to discontinue operation of the column and remove and clean the packing before reintroducing it so that the reaction can continue. Furthermore, after the packing has been cleaned and replaced, it is sometimes necessary to reinoculate it with the desired microorganism. However, even in those instances where this is not necessary, one finds that the packing particles are so thoroughly remixed that the stratification of specific colonies of microorganisms is destroyed. In either case, an appreciable period of time is required to re-establish the previous equalibrated stratification, resulting in lower productivity and higher costs.

DISCLOSURE OF THE INVENTION

In the light of the foregoing, therefore, it is a first aspect of this invention to provide continuing high reaction efficiencies in a continuous microbiological process.

A second aspect of the invention is to promote reaction efficiencies by providing an apparatus and method for removing column-plugging debris, as required, with minimal disruption of the reaction.

Another aspect of the invention disclosed herein is the provision of a column where continuous microbiological processes may be conducted, which can be cleaned without removing the packing therefrom.

A further aspect of the invention is to maintain specialized colonies of microorganisms in stratified zones both before and after cleaning of the column and its packing has been accomplished.

A still further aspect of the invention disclosed is the design of a specially designed packed column, and provision of a method for operating it, which allows re-establishment of the stratified orientation of specialized microbiological colonies following cleaning of the packing and the column, so that such orientation is substantially the same following such cleaning, as prior to it.

The preceding and other aspects are provided by a bioreactor for carrying out microbiological reactions comprising a vertical hollow column containing column packing comprising particles classifiable by means of differential liquid settling rates, said column having a lower reaction section, and an upper disengagement section, said disengagement section having a volume at least about as large as the volume of said reaction section, said packing being disposed in said column so that when a microbiological reaction is taking place in said column, said column packing is located in said reaction section, and when said column packing is being regenerated, said column packing is substantially located in said disengagement section, and wherein said column includes a reactant inlet near one end, and a product outlet near the other end.

Additional aspects of the invention are provided by a process for conducting microbiological reactions in a vertical hollow column containing column packing particles classifiable by means of differential liquid settling rates, said column having a lower reaction section, and an upper disengagement section, as well as a reactant inlet near one end, and a product outlet near the other end, comprising the following sequential steps:

(1) Continuously introducing a classifying liquid near the bottom end of the column and continuously removing said liquid near the top end of the column at a flow rate such that the upward linear velocity of said liquid exceeds the linear settling rate of said column packing particles, and maintaining the flow rate until said column packing particles have been substantially dispersed within said disengagement section;

(2) Thereafter, gradually reducing the flow rate so that said particles slowly settle into the column's reaction section, thereby classifying said packing particles in an initial classified condition;

(3) Exposing said packing particles to an inoculant containing the selected bioreaction microorganisms;

(4) Continuously introducing a liqiud feed comprising microorganism nutrients into a reactant inlet located near the bottom end of said column at a substantially constant flow rate such that its upward linear velocity is below the linear settling rate of said packing particles, and continuously removing product and unreacted feed from a product outlet located near the top end of said column;

(5) Wherein when column fouling has progressed to a determined point, the column is cleaned by increasing the flow rate so as to provide an upward linear velocity beyond the linear settling rate of said packing particles, until said packing particles have been substantially dispersed within said disengagement section;

(6) Thereafter, maintaining the flow rate at the point which its upward linear velocity is such as to cause said packing particles to remain substantially suspended in such dispersed state within the disengagement section until the desired amount of fouling has been removed from the packing particles, and from the column;

(7) Thereafter, gradually reducing the flow rate below the linear settling rate of said packing particles so that said packing particles slowly settle into the column's reaction section, substantially oriented in the initial classified condition;

(8) Re-establishing the feed flow rate of step (4), and (9) Repeating step (5) et seq. as required to maintain the desired bioreaction.

BRIEF DESCRIPTION OF THE DRAWINGS

The invention will be better understood when reference is had to the following figures in which.

BEST MODE FOR CARRYING OUT THE INVENTION

Figure 1:
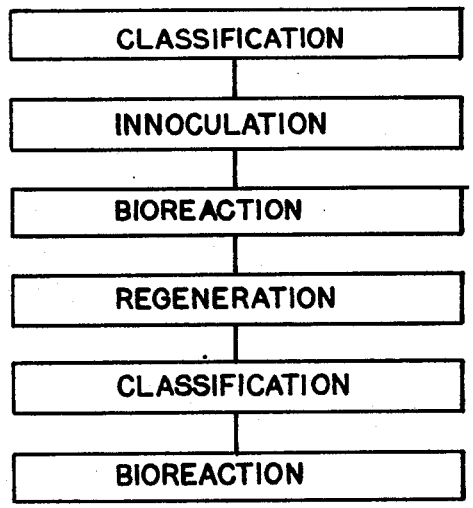
FIG. 1 is a block diagram of steps involved in carrying out the process of the invention.

FIG. 1 is a block diagram showing the sequence of operating steps of the invention disclosed. When a bioreactor of the type contemplated by the invention is operated, it is necessary that the packing particles employed be of a type which may be classified, based upon their different settling rates in a liquid. Generally speaking, except for those of colloidal size, particles having freedom of movement in a liquid settle at a substantially constant velocity which is determined both by the diameter of the particles, as well as their density. Consquently, by selecting a spectrum of packing particles representing different particle diameters, densities, or both, it is possible to repeatedly classify the particles in the same order by allowing them to slowly settle in a liquid. This fact is the basis of the invention disclosed.

Packing of the type described, comprising particles having differing settling rates, is placed in the bioreactor, and a liquid such as water, or the feed to be employed in the bioreaction, is passed upward through the packing at a rate sufficient to assure an upward linear velocity in excess of the settling rate of the various packing particles. After the packing particles have been dispersed in the column, the rate is gradually reduced to a velocity which allows the particles to gradually settle. It will be found that packing materials thus processed will have classified themselves, the more rapidly settling particles being deposited toward the bottom of the column, while the slower settling particles will progressively settle nearer the top. Those settling at intermediate velocities will arrange themselves in between, depending upon their relative velocities. Furthermore, particles of the type described will rearrange themselves substantially in identical fashion every time they are classified in the manner. described.

Packing particles suitable for the invention may be selected from many different materials, such as plastic particles, gravel of different sizes or density, zirconia beads, glass beads, glass beads with incorporated bubbles of air, particles of alumnia of varying porosity, hollow spheres with different wall thickness, beryl saddles, and various other similar materials. While the shape of the particles may vary, it is desirable that they not have a configuration which causes adjacent particles to interlock, a phenomenon which would tend to hamper efficient classification. The size of the packing particles may vary widely and still be capable of classification as described. It has been found, however, that the use of substantially spherical particles is of advantage, and such particles having a diameter of from about 5-10 mesh are particularly adaptable to classification in the packed column of the invention. The relative amounts of particles having differing densities and/or diameters will depend upon the number of vertical zones desired within the column to provide for microorganism colonies having similar characteristics. Normally, it is preferred to provide from about 2-10 distinct colonies of microorganisms; consequently, the diameters and density of the packing will be chosen so that the column packing will form that number of vertical zones, usually equal in height, following classification.

Although the packing particles may be used without preliminary preparation, it is frequently useful to pretreat them to improve the ability of the microorganisms which employ the particles as a supporting substrate to adhere to them. This may be done in a variety of ways, such as mechanically abrading their surface to improve mechanical adhesion, or by chemical treatment, as for instance, by treating glass particles with hydrofloric acid. Likewise, the selection of column packing particles having a naturally porous conformation provides certain advantages. Other techniques that may be used include treating the particles with a proteinpolyelectrolyte mixture, subsequently crosslinked on the packing surface with glutaraldehyde, ethylchloroformate, or formaldehyde, thereby creating a thin, insoluble hydrophillic coating on the particles. Still another technique involves reacting the surface of ceramic particles with a silane coupling compound containing active functional groups, e.g., an amine, epoxy, or carboxyl group.

Inoculation of the packing material may be accomplished in a variety of ways. It can be done by contacting the particles with a liquid containing the microorganisms; or the microorganisms may be applied to the particles as a solid, for example, in the form of a powder. The microorganisms may be selected from a wide variety of types such as kefir-derived cultures, i.e., microbial ecosystems stable for protracted periods under primitive culture conditions, including latic acid, denitrifying, methane, or mixed volatile acid forming cultures, other bacteria, yeasts, enzymes, and the like. When the microorganisms consist of bacteria, either those of the anaerobic or aerobic type may be used. One particularly convenient way for inoculating the packing material is to circulate a "beer" of the microorganisms in a liquid nutrient through the packing material after it has been classified in the column.

Following inoculation, the bioreaction is commenced by introducing a liquid nutrient feed into the column. In the case of anaerobic bacteria, the feed will normally be introduced near the bottom of the column and withdrawn near its top, assuring that the microorganism containing packing is immersed at all times under the nutrient liquid. In the case of aerobic bacteria, the feed will generally be introduced near the top of the column and allowed to trickle downward over the packing particles, following which it is withdrawn near the column's bottom. When the column is run in a down-flow, aerobic mode, it will usually be desirable to provide an upward, countercurrent flow of sterile air or other oxygen containing gas. Feed rates may vary, so long as they are such that when the column is operated in the upflow mode, the upward linear velocity of the feed does not exceed the settling rate of the packing particles. Furthermore, it is desirable that the flow be maintained slowly enough so that turbulence and accompanying localized recirculation is avoided, since this would tend to defeat the objective of establishing distinct microorganism colonies in the different packing zones. In addition, a feed rate once established should be maintained so that the different colonies of microorganisms can adapt to specific conditions of nutrient and product concentrations which exist in their particular zones. In the case of bioreactions conducted with a column operated in a down-flow mode, the feed rate is ordinarily adjusted so that at least about 75% of the space in the packed section of the column will be in an empty or void condition.

Suitable nutrient feed will depend upon the nature of the microorganisms and the product desired; however, sugar containing liquids, waste materials such as urban waste and food canning wastes, nitrogen containing liquids, and similar feeds are typical. Frequently, reaction conditions such as pH, product, nutrient concentrations, and the like are monitored at various points along the column. If desired, supplemental nutrients may also be introduced along the length of the column. These may include, for example, such things as vitamins, minerals, pH adjusting substances, for example, acetic acid, sodium bicarbonate, etc., or other substances required to maintain the microorganisms in a healthy, active state.

At some point after the introduction of feed has commenced, it will be found that the column equilibrates and distinct colonies of microorganisms will have developed, compatible with the feed and product concentrations existing in their specific zone. Operation of the bioreactor will be continued until visible evidence of flow restriction, channeling, or related undesirable occurance is noted. This is readily, visually apparent in the case of the preferred column, fabricated from glass, although it may also be deduced from reduced flow rates, increased pressure drops, and similar phenomona. Typically, fouling of the type described can occur in from about 1-7 days, and oftentimes takes the form of mold-like growths which form on the column packing. At such point the bioreaction is discontinued and the column packing is regenerated.

Regeneration is accomplished by introducing the liquid nutrient or a sterile liquid such as water near the bottom of the column at a rate such that the upward linear velocity of the liquid through the column exceeds the linear settling rate of the column packing. The packing particles are thereupon dislodged from the reaction section of the column and rise into the disengagement section where they are held until most of the contaminating fouling has been dislodged. The dislodgement process is often accelerated by providing an agitator in the disengagement section capable of producing a turbulent condition. The use of a column transition section extending from the top of the reaction section to a disengagement section having a larger diameter than the reaction section is desirable since the varying cross-sectional areas thus obtained provide varying linear velocities of liquids passing through them, enabling the more rapidly settling particles, as well as the slower settling ones to be maintained in suspension at a particular feed rate. The regeneration or washing cycle is continued for only as long as necessary to remove the desired amount of contaminant in order to minimize the time of disruption of the environment preferred by the different colonies of microorganisms present. In addition, an oxygenated liquid is normally used when the column packing involved is that employed in connection with an aerobic process. The wash liquid is withdrawn near the top of the column, and if desired, it may be recycled to the bottom of the column following removal of the fouling contaminant. Inspection of the effluent wash liquid for contaminant provides an indication of when the regeneration process is complete. At such point, the feed flow rate to the bottom of the column is slowly reduced until its linear velocity in the column falls below the linear velocity of the particles' settling rates, resulting in classification of the column packing back into the reaction zone.

Because the microorganisms representing a specific colony were developed on particular column packing particles characterized by a specific settling rate, it will be found that in the process of reclassification, such distinct colonies are reformed at their former location in the column, thus preserving the identity of the colony. After the classification has been completed, the original feed flow rate is re-established, permitting the reaction to continue as before, but without any need for a time-consuming equilibrium period to allow specific colonies of microorganisms to develop.

Figure 2:
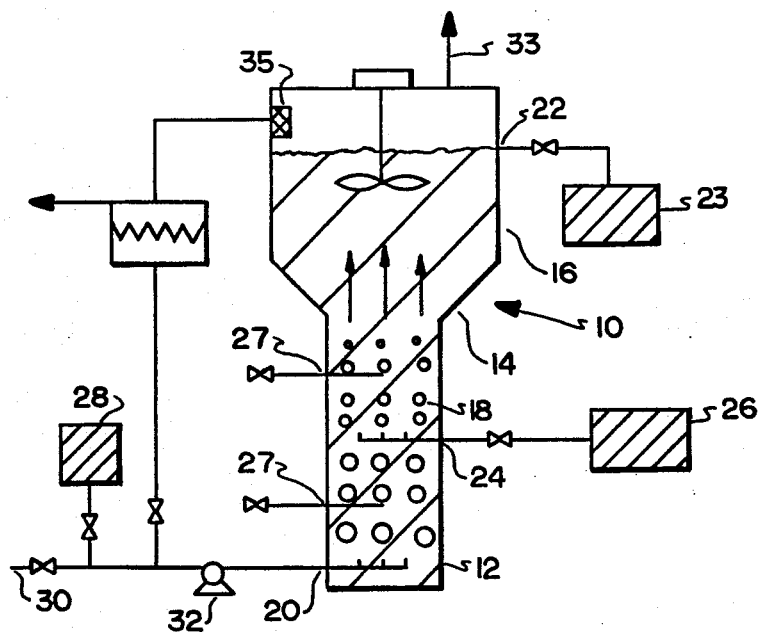
FIG. 2 is a semischematic diagram of an apparatus of the invention, including associated components, in which the bioreaction in progress is being operated in an upflow mode.

FIG. 2 is a semischematic representation of an upflow bioreactor 10 comprising a reaction section 12, a transition section 14, and a disengagement section 16. The bioreactor 10, filled with column packing particles 18, is termed an "up-flow" bioreactor because feed enters it at reactant inlet 20, and proceeds up the column to product outlet 22 where it leaves the column, proceeding to product storage area 23. As previously indicated, one or more intermediate feed points 24 can be located between the reactant inlet 20 and product outlet 22, and desired supplemental materials may be introduced from storage point 26. One or more sampling points 27 may also be located between the reactant inlet 20 and product outlet 22. Reactant nutrient feed from feed storage 28, or a different liquid, for example, sterile water entering from auxiliary inlet 30, may be fed into the column by means of a pump 32. The removal of gases generated during the bioreaction, or those added in the case of an aerobic reaction, is accomplished by means of gas vent 33. While a column in which the reaction section 12 and the disengagement section 16 have the same cross-section may be used, particularly in conjunction with a retaining screen 35 to prevent column packing particles with slower settling rates from leaving the column during the regeneration step, the use of a transition section 14 is preferrable. Commonly, the transistion section 14 will take the form of an inverted truncated cone, the diameter at the base of which is the same as the diameter of the disengagement section 16, while the top of the cone will have a diameter equal to the diameter of the reaction section 12. Since a primary purpose of a conical transistion section is to provide differential linear felocities, the angle of the cone is relatively unimportant, and in any event, will depend upon the nature of the packing material employed. The angle of the cone should be steep enough to prevent the accumulation of packing material along its inside wall, while at the same time shallow enough to provide enough difference in linear velocity of the liquid passing through it to substantially suspend both slow settling particles near its top, and fast settling packing particles near its bottom during the regeneration cycle. The dimensions of the reaction section may vary as desired, and will depend upon the throughput desired as well as the nature of the column packing material employed, the number of zones to be formed, and similar considerations.

Figure 2A:
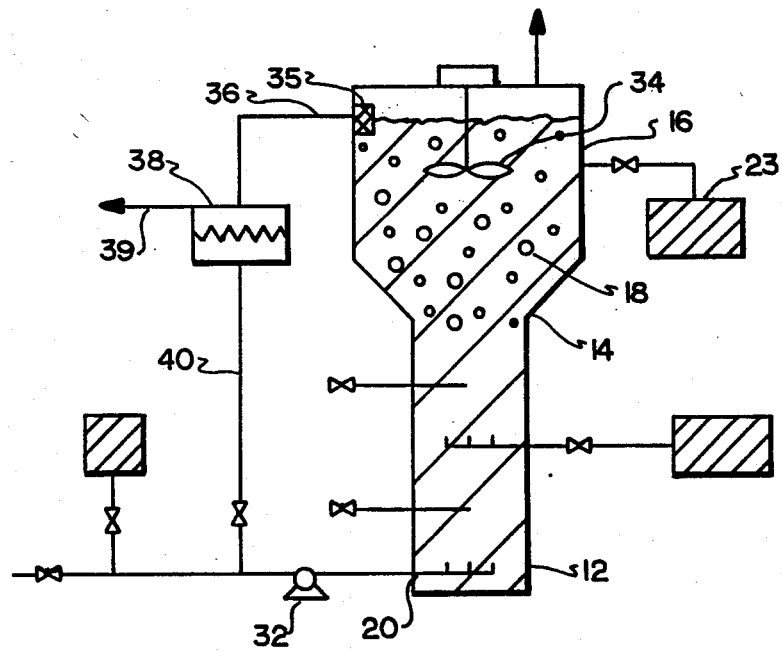
FIG. 2A is a semischematic diagram of FIG. 2 in which the bioreaction has been temporarily discontinued in order to permit the column packing to be regenerated, the process of which is illustrated.

FIG. 2A is a semischematic representation of a bioreactor during regeneration of the column packing particles. In the Figure, the feed rate has been increased to the point at which it's linear velocity exceeds the settling rate of column packing 18, and a substantial amount of the packing has left the reaction section 12 and entered transition section 14, and disengagement section 16, where it will remain dispersed during the regenerative packing cleaning process. Disengagement of the contaminating fouling is desirably accelerated by the turbulence promoted by agitator 34 during the regeneration process. Column access to product storage 23 is blocked during regeneration, and the wash liquid is forced to leave the column at regeneration outlet 36, from where it proceeds to separator 38. In separator 38, the contaminates 39 are removed from the wash liquid, which may be recycled through recycle system 40 back into the column by means of pump 32 and reactant inlet 20. While the column may be made of different materials, the use of glass has been found to be particularly advantageous, since it permits observations of the classification process, as well as progress of the reaction, and the regeneration process. The positioning of the components shown in the Figure is merely for the purpose of illustration, however, it being possible to change various of the components, and their position, without departing from the spirit of the invention.

Figure 3:
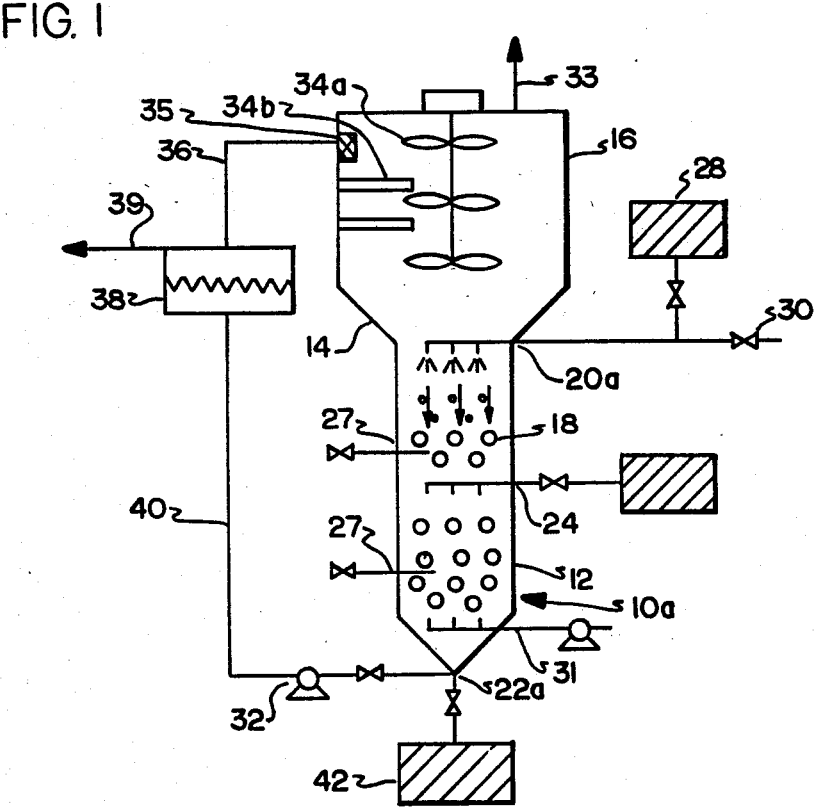
FIG. 3 is a semischematic diagram of an apparatus of the invention in which a microbiological reaction is being conducted in a downflow manner.

FIG. 3 shows the semischematic representation of a downflow bioreactor 10(a). As in the case of FIG. 2, the column consists of a reaction section 12, filled with column packing 18, a transition section 14, and a regeneration section 16. During the bioreaction, feed to the column enters the column from feed storage 28 through reactant inlet 20(a) and trickles down the column packing 18, eventually leaving at product outlet 22(a) on its way to product storage 42. Desirably, since the downflow reaction involves aerobic microorganisms, an oxygen containing gas such as sterile air is introduced at air inlet 31, passing up through column packing 18, and eventually leaving the column at gas vent 33. As in the case of the upflow bioreactor 10, the column 10 may be fitted with sample points 27, and intermediate feed points 24. During the regeneration cycle, feed from feed storage 28, or a different liquid such as sterile water entering at auxiliary inlet 30, is introduced in an amount sufficient to fill the reactor to regeneration outlet 36. A multiblade agitator 34(a), in combination with baffle fingers 34(b), is shown in the Figure, serving the purpose of creating fouling removing turbulence from the column packing particles. Liquid leaves the column at regeneration outlet 36 on its way to separator 38, which may be a contaminant separating filter device suitable for the purpose. After the liquid has been separated from the contaminating fouling 39 in separator 38, it enters recycle system 40 where it is returned to the bottom of the column at product outlet 22(a) by pump 32.

The invention is illustrated still further by the following examples:

EXAMPLE 1

A vertical glass tube, two inches in diameter and two feet long, fitted at its lower end with a liquid feed inlet, is provided at its upper end with a separator of the type customarily used with fluidized bed operations. The separator, which serves the purpose of a disengaging section, has a volume about twice that of the reaction tube section. A mixture of column packing particles is prepared from approximately equal amounts of four millimeter glass beads having three different densities, which have been coated with gelatin cross-linked with formaldehyde. The packing mixture is then introduced into the reaction tube of the apparatus, and distilled water is fed into the bottom of the tube at a rate sufficient to cause the packing material to disperse into the separator section. The rate is thereafter slowly reduced, causing the gradual settling of the packing into the reaction tube in a classified order.

An inoculant mixture is then prepared which contains on a weight percent basis about 1% yeast extract, 26% anhydrous glucose, and 73% water. The mixture is maintained at 70° F. until fermentation is clearly evident, after which it is introduced into the bottom of the reaction tube at a rate sufficient to provide a retention time within the tube of about ½ hours. When the inoculant mixture has been fed for about four hours, the feed is shifted to a solution containing about 26% by weight glucose in water. After four hours, analysis of the liquid leaving the top of the reaction tube shows an ethanol concentration of about 15%, and indicates a glucose consumption of approximately 98%. The apparatus is operated under the conditions stated until there is visible evidence of flow restriction, due to the build-up of residual organic material in the reactor. At this point, the feed rate is increased to a rate at which the column packing particles disperse into the separator section of the apparatus, where solid fragments of contaminant are broken off the packing. The solids containing liquid is directed onto a collection filter where the contaminant is separated, and from which the filtrate is recycled to the bottom of the reaction tube. The higher rate of flow is continued until only a thin layer of organic material remains on the packing to serve as a starter inoculant. The wash flow is then gradually reduced below the settling rate of the packing particles, providing packing particles classification in the reaction tube in substantially the original order. The nutrient feed is thereafter resumed at the original flow rate period, re-establishing the reaction.

EXAMPLE 2

The apparatus of Example 1 is used in a fermentation of whey in which, however, the packing material is first treated with an epoxy silane coupling agent in alcohol. The packing is then dried and slurried in a 2% gelatin mixture for about three hours. Packing thus prepared is placed in the apparatus and classified with distilled water in the manner described in Example 1. The inoculant is prepared from a kefir derived culture mixtured with cottage cheese whey, characterized by a 5% solids content. The inoculant mixture is thereafter passed into the bottom of the reactor at a rate such that a retention time of approximately ½ hour is obtained. After four hours time, the inoculant feed is discontinued, and a feed of whey without added culture is fed for an additional period of four hours, at which point the effluent is found to contain about 2.4% by weight of lactic acid. After operating the reaction under the conditions described for about 48 hours, evidence of a biological buildup on the column packing is observed. The whey feed is then discontinued and distilled water is introduced at the bottom of the column at a rate which results in the fluidization of the packing, and its substantial transfer into the separator-disengagement section. In the separator, a power stirrer is used to accelerate the dislodgement of biological solids from the packing, a process requiring about three minutes. The flow rate is thereafter slowly reduced over a period of about two minutes to restore the original classified packing bed order. The introduction of whey feed is then resumed at the original rate, and at the end of about one hour, analysis shows that lactic acid production has returned to the rate achieved prior to the regeneration operation.

While in accordance with the patent statutes a preferred embodiment and best mode has been presented, the scope of the invention is not limited thereto, but rather is to be measured by the scope of the attached claims.

What is claimed is:

1. A process for conducting microbiological reactions in a vertical hollow containing column packing particles classifiable by means of differential liquid settling rates, said column having a lower reaction section in which said microbiological reactions take place, and an upper disengagement section in which said packing particles can be dispersed and in which separation of biological fouling from said packing particles occurs, said upper disengagement section having a larger cross-sectional area than said lower reaction section, as well as a reactant inlet near one end, and a product outlet near the other end, comprising the following sequential steps:
   (1) continuously introducing a liquid near the bottom end of the column and continuously removing said liquid near the top end of the column at a flow rate such that its upward linear velocity exceeds the settling rate of said column packing particles, and maintaining the flow rate until said column packing particles have been substantially dispersed within said disengagement section;
   (2) thereafter, gradually reducing the flow rate so that sai particles slowly settle into the column's reaction section, thereby classifying said packing particles in an initial classified condition in which faster settling packing particles are located toward the lower end of said reaction section, while slower settling packing particles are located toward the upper end of said reaction section;
   (3) exposing said packing particles to an inoculant containing selected bioreaction microorganisms;
   (4) continuously introducing a liquid feed comprising microorganism nutrients into a reactant inlet near the bottom end of said column at a substantially constant flow rate such that its upward linear velocity is insufficient to suspend said packing particles, and continuously removing product and unreacted feed from a product outlet located near the top end of said column;
   (5) wherein when packing particle fouling has progressed to a determined point, the column is cleaned by increasing the flow rate of a liquid through the column so as to provide an upward linear velocity sufficient to prevent the settling of said packing particles, until said packing particles have been substantially dispersed within said disengagement section;
   (6) thereafter, maintaining said flow rate at the point at which its upward linear velocity is sufficient to prevent the settling of said packing particles, allowing them to remain substantially suspended in such dispersed state within the disengagement section until the desired amount of said fouling has been removed from the packing particles, and from the column;
   (7) thereafter gradually reducing the flow rate below the linear settling rate of said packing particles, allowing them to slowly settle into the column's reaction section substantially oriented in the initial classified condition in which said faster settling particles are located toward the lower end of said reaction section, while said slower settling particles are located toward the upper end of said reaction section; and
   (8) reestablishing the biological reaction using the process of step (4).

2. The process according to claim 1 in which said column is cylindrical in shape and in which said disengagement section has a diameter greater than said reaction section, and a volume about at least as great, and wherein such sections are joined by a transition section having the shape of an inverted truncated cone, the base of which forms the bottom of the disengagement section, and the top of which forms the top of the reaction section.

3. The process according to claim 2 in which at least one feed point is located between the reactant outlet near the bottom end of the column, and the product outlet near the top end of the column.

4. A process for conducting microbiological reactions in a vertical hollow column containing column packing particles classifiable by means of differential liquid settling rates, said column having a lower reaction section in which said microbiological reactions take place, and an upper disengagement section in which said packing particles can be dispersed and in which separation of biological fouling from said packing particles occurs, said upper disengagement section having a larger cross-sectional area than said lower reaction section, as well as a reactant inlet near one end, and a product outlet near the other end, comprising the following sequential steps:

(1) continuously introducing a liquid near the bottom end of the column and continuously removing said liquid near the top end of the column at a flow rate such that its upward linear velocity exceeds the settling rate of said column packing particles, and maintaining the flow rate until said column packing particles have been substantially dispersed within said disengagement section;

(2) thereafter, gradually reducing the flow rate so that such particles slowly settle into the column's reaction section, thereby classifying said particles in an initial classified condition in which faster settling packing particles are located toward the lower end of said reaction section, while slower settling packing particles are located toward the upper end of said reaction section;

(3) exposing said packing particles to an inoculant containing selected bioreaction microorganisms;

(4) continuously introducing a liquid feed comprising microorganism nutrients into a reactant inlet located near the top en of said column at a substantially constant flow rate, and continuously removing product and unreacted feed from a product outlet located near the bottom end of said column at the same flow rate;

(5) wherein when packing particles fouling has progressed to a determined point, the column is cleaned by introducing a liquid into the column at its bottom end at a flow rate so as to provide an upward linear velocity sufficient to prevent the settling of said packing particles, until said packing particles have been substantially dispersed within said disengagement section;

(6) thereafter, maintaining said flow rate at the point at which its upward linear velocity is sufficient to prevent the settling of said packing particles, allowing them to remain substantially suspended in such dispersed state within the disengagement section until the desired amount of said fouling has been removed from the packing particles, and from the column;

(7) thereafter gradually reducing the flow rate below the linear settling rate of said packing particles, allowing them to settle slowly into the column's reaction section substantially oriented in the initial classified condition in which said faster settling particles are located toward the lower end of said reaction section, while said slower settling particles are located toward the upper end of said reaction section; and (8) reestablishing the biological reaction using the process of step (4).

5. A process according to claim 4 in which at least one feed point is located between the reactant inlet near the top end of the column and the product outlet near the bottom end of the column.

6. A process for conducting microbiological reactions in a vertical hollow column containing column packing particles classifiable by means of differential liquid settling rates, and inoculated with selected bioreaction organisms by exposure thereto prior to said reactions, said column having a lower reaction section in which said microbiological reactions take place, and an upper disengagement section in which said packing particles can be dispersed and in which separation of biological fouling from said packing particles occurs, said upper disengagement section having a larger cross-sectional area than said lower reaction section, as well as a reactant inlet near one end, and a product outlet near the other end, comprising the following sequential steps:

(1) continuously introducing a liquid near the bottom end of the column and continuously removing said liquid near the top end of the column at a flow rate such that its upward linear velocity exceeds the settling rate of said column packing particles, and maintaining the flow rate until said column packing particles have been substantially dispersed within said disengagment section;

(2) thereafter, gradually reducing the flow rate so that said particles slowly settle into the column's reaction section, thereby classifying said packing particles in an initial classified condition in which faster settling packing particles are located toward the lower end of said reaction section, while slower settling packing particles are located toward the upper end of said reaction section;

(3) continuously introducing a liquid feed comprising microorgangism nutrients into a reactant inlet near the bottom end of said column at a substantially constant flow rate such that its upward linear velocity is insufficient to suspend said packing particles, and continuously removing product and unreacted feed from a product outlet located near the top end of said column;

(4) wherein when packing particle fouling has progressed to a determined point, the column is cleaned by increasing the flow rate of a liquid through the column so as to provide an upward linear velocity sufficient to prevent the settling of said packing particles, until said packing particles have been substantially dispersed within said disengagement section;

(5) thereafter, maintaining said flow rate at the point at which its upward linear velocity is sufficient to prevent the settling of said packing particles, allowing them to remain substantially suspended in such dispersed state within the disengagement section until the desired amount of said fouling has been removed from the packing particles, and from the column;

(6) thereafter gradually reducing the flow rate below the linear settling rate of said packing particles, allowing them to slowly settle into the column's reaction section substantially oriented in the initial classified condition in which said faster settling particles are located toward the lower end of said reaction section, while said slower settling particles are located toward the upper end of the said reaction section; and (7) reestablishing the biological reaction using the process of step (3).

7. A process for conducting microbiological reactions in a vertical hollow column containing column packing particles classifiable by means of differential liquid settling rates, and inoculated with selected bioreaction organisms by exposure thereto prior to said reactions, said column having a lower reaction section in which said microbiological reactions take place, and an upper disengagement section in which said packing particles can be dispersed and in which separation of biological fouling from said packing particles occurs, said upper disengagement section having a larger cross-sectional area than said lower reaction section, as well as a reactant inlet near one end, and a product outlet near the other end, comprising the following sequential steps:

(1) continuously introducing a liquid near the bottom end of the column and continuously removing said liquid near the top end of the column at a flow rate such that its upward linear velocity exceeds the settling rate of said column packing particles, and maintaining the flow rate until said column packing particles have been substantially dispersed within said disengagement section;

(2) thereafter, gradually reducing the flow rate so that such particles slowly settle into the column's reaction section, thereby classifying said particles in an initial classified condition in which faster settling packing particles are located toward the lower end of said reaction section, while slower settling packing particles are located toward the upper end of said reaction section;

(3) continuously introducing a liquid feed comprising microorganisms nutrients into a reactant inlet located near the top end of said column at a substantially constant flow rate, and continuously removing product and unreacted feed from a product outlet located near the bottom end of said column at the same flow rate;

(4) wherein when packing particles fouling has progressed to a determined point, the column is cleaned by introducing a liquid into the column at its bottom end at a flow rate so as to provide an upward linear velocity sufficient to prevent the settling of said packing particles, unit said packing particles have been substantially dispersed within said disengagement section;

(5) thereafter, maintaining said flow rate at the point at which its upward linear velocity is sufficient to prevent the settling of said packing particles, allowing them to remain substantially suspended in such dispersed state within the disengagement section until the desired amount of said fouling has been removed from the packing particles, and from the column;

(6) thereafter gradually reducing the flow rate below the linear settling rate of said packing particles, allowing them to settle slowly into the column's reaction section substantially oriented in the initial classified condition in which said faster settling particles are located toward the lower end of said reaction section, while said slower settling particles are located toward the upper end of said reaction section; and (7) reestablishing the biological reaction using the process of step (3).

* * * * *